(12) United States Patent
Grey et al.

(10) Patent No.: US 8,047,987 B2
(45) Date of Patent: Nov. 1, 2011

(54) BLADE INSERT ILLUMINATOR

(75) Inventors: Thomas L. Grey, San Marcos, CA (US);
Alex Vayser, San Marcos, CA (US);
Jonathan G. Gasson, San Marcos, CA (US)

(73) Assignee: Invuity, Inc., San Francisco, CA (US)

( * ) Notice: Subject to any disclaimer, the term of this patent is extended or adjusted under 35 U.S.C. 154(b) by 992 days.

(21) Appl. No.: 11/805,682

(22) Filed: May 23, 2007

(65) Prior Publication Data

US 2007/0293729 A1 Dec. 20, 2007

Related U.S. Application Data

(60) Provisional application No. 60/808,877, filed on May 26, 2006.

(51) Int. Cl.
*A61B 1/32* (2006.01)

(52) U.S. Cl. .......................................... 600/245

(58) Field of Classification Search .................. 600/199, 600/200, 203, 212, 213, 223, 241, 245, 246
See application file for complete search history.

(56) References Cited

U.S. PATENT DOCUMENTS

| | | | |
|---|---|---|---|
| 1,246,339 A | 11/1917 | Isaac | |
| 1,326,300 A | 12/1919 | Smit | |
| 2,186,143 A | 1/1940 | Neugass | 128/16 |
| 2,235,979 A | 3/1941 | Brown | 128/6 |
| 2,247,258 A | 6/1941 | Shepard | 128/16 |
| 2,482,971 A | 9/1949 | Golson | 128/6 |
| 3,075,516 A | 1/1963 | Strauch | 128/6 |
| 3,261,350 A | 7/1966 | Wallace | 128/6 |
| 3,328,570 A | 6/1967 | Balchunas | 240/2.1 |
| 3,590,232 A | 6/1971 | Sadowski | 240/2 |
| 3,638,644 A | 2/1972 | Reick | 128/16 |
| 3,664,330 A | 5/1972 | Deutsch | 128/18 |
| 3,680,546 A | 8/1972 | Asrican | 128/18 |
| 3,712,705 A | 1/1973 | Marcatili | 350/96 |
| 3,807,393 A | 4/1974 | McDonald | 128/20 |
| 3,829,675 A | 8/1974 | Mariani | 240/1 |
| 3,890,960 A | 6/1975 | Wunsch et al. | 128/16 |
| 3,892,959 A | 7/1975 | Pulles | 240/1 |
| 3,901,674 A | 8/1975 | Strack et al. | 65/3 |
| 3,950,073 A | 4/1976 | Horiguchi et al. | 350/96 |
| 4,023,903 A | 5/1977 | Scheib | 355/71 |
| 4,043,636 A | 8/1977 | Eberhardt et al. | 350/160 |
| 4,052,980 A | 10/1977 | Grams et al. | 128/18 |
| 4,173,392 A | 11/1979 | Ekinaka et al. | 350/96.26 |
| 4,226,228 A | 10/1980 | Shin et al. | 128/20 |

(Continued)

FOREIGN PATENT DOCUMENTS

GB 1242374 8/1971

(Continued)

*Primary Examiner* — Thomas C. Barrett
*Assistant Examiner* — Sameh Boles
(74) *Attorney, Agent, or Firm* — Wilson Sonsini Goodrich & Rosati

(57) ABSTRACT

A blade insert illumination system includes one or more illumination elements composed of a transparent or semi-transparent polymer that is preferably biocompatible and sterilizable. The illumination elements operate as a waveguide and may incorporate optical components such as, for example, facets, lenses, gratings, prisms and or diffusers to operate as precision optics for customized delivery of the light energy. The illumination elements may be modular, allowing components to be mixed and matched for different sizes of blade retractors, or may be a single integrated unit.

8 Claims, 9 Drawing Sheets

U.S. PATENT DOCUMENTS

| | | | | |
|---|---|---|---|---|
| 4,257,084 A | 3/1981 | Reynolds | | 362/31 |
| 4,300,541 A | 11/1981 | Burgin | | 128/18 |
| 4,306,546 A | 12/1981 | Heine et al. | | 128/6 |
| 4,337,763 A | 7/1982 | Petrassevich | | 128/20 |
| 4,471,412 A | 9/1984 | Mori | | 362/32 |
| 4,500,181 A | 2/1985 | Takahashi | | 350/574 |
| 4,562,832 A | 1/1986 | Wilder et al. | | 128/20 |
| 4,597,030 A | * 6/1986 | Brody et al. | | 362/572 |
| 4,616,635 A | 10/1986 | Caspar et al. | | 128/20 |
| 4,630,895 A | 12/1986 | Abdala, Jr. et al. | | 350/345 |
| 4,686,972 A | 8/1987 | Kurland | | 128/92 |
| 4,714,983 A | 12/1987 | Lang | | 362/27 |
| 4,733,332 A | 3/1988 | Yamashita et al. | | 362/32 |
| 4,765,701 A | 8/1988 | Cheslak | | 350/96.1 |
| 4,785,796 A | 11/1988 | Mattson | | 128/9 |
| 4,790,751 A | 12/1988 | Reinhardt et al. | | 433/29 |
| 4,790,752 A | 12/1988 | Cheslak | | 433/37 |
| 4,802,460 A | 2/1989 | Ohkuwa et al. | | 128/6 |
| 4,807,599 A | 2/1989 | Robinson et al. | | 128/16 |
| 4,885,663 A | 12/1989 | Parker | | 362/32 |
| 4,897,771 A | 1/1990 | Parker | | 362/298 |
| 4,905,082 A | 2/1990 | Nishigaki et al. | | 358/98 |
| 4,907,132 A | 3/1990 | Parker | | 362/32 |
| 4,968,124 A | 11/1990 | Deckert et al. | | 350/574 |
| 4,974,122 A | 11/1990 | Shaw | | 362/31 |
| 5,005,108 A | 4/1991 | Pristash et al. | | 362/31 |
| 5,035,232 A | 7/1991 | Lutze et al. | | 128/20 |
| 5,039,198 A | 8/1991 | VanBeek | | 385/117 |
| 5,052,778 A | 10/1991 | Jamshid | | 385/125 |
| 5,097,396 A | 3/1992 | Myers | | 362/32 |
| 5,136,480 A | 8/1992 | Pristash et al. | | 362/31 |
| 5,159,921 A | 11/1992 | Hoover | | 128/20 |
| 5,165,387 A | 11/1992 | Woodson | | 128/6 |
| 5,207,493 A | 5/1993 | Murase et al. | | 362/31 |
| 5,209,757 A | 5/1993 | Krug et al. | | 606/162 |
| 5,226,105 A | 7/1993 | Myers | | 385/147 |
| 5,237,985 A | 8/1993 | Hodgson et al. | | 128/17 |
| 5,281,134 A | 1/1994 | Schultz | | 433/29 |
| 5,295,216 A | 3/1994 | Halter | | 385/120 |
| 5,303,323 A | 4/1994 | Mezei | | 385/147 |
| 5,307,245 A | 4/1994 | Myers et al. | | 362/32 |
| 5,312,569 A | 5/1994 | Mezei | | 264/1.5 |
| 5,312,570 A | 5/1994 | Halter | | 264/1.5 |
| 5,334,150 A | 8/1994 | Kaali | | 604/164 |
| 5,353,786 A | 10/1994 | Wilk | | 128/23 |
| 5,354,302 A | 10/1994 | Ko | | 606/104 |
| 5,377,084 A | 12/1994 | Kojima et al. | | 362/31 |
| 5,390,085 A | 2/1995 | Mari-Roca et al. | | 362/31 |
| 5,394,863 A | 3/1995 | Sanford et al. | | 128/3 |
| 5,400,773 A | 3/1995 | Zhu et al. | | 128/20 |
| 5,431,153 A | 7/1995 | Lee | | 600/183 |
| 5,432,876 A | 7/1995 | Appeldorn et al. | | 385/31 |
| 5,441,041 A | 8/1995 | Sauer et al. | | 600/106 |
| 5,445,142 A | 8/1995 | Hassler, Jr. | | 600/105 |
| 5,448,990 A | 9/1995 | De Faria-Correa | | 600/129 |
| 5,467,208 A | 11/1995 | Kokawa et al. | | 359/49 |
| 5,499,912 A | 3/1996 | Mezei | | 425/363 |
| 5,520,611 A | 5/1996 | Rao et al. | | 600/245 |
| 5,521,342 A | 5/1996 | Bartley et al. | | 200/5 |
| 5,521,797 A | 5/1996 | Kashima et al. | | 362/31 |
| 5,562,696 A | 10/1996 | Nobles et al. | | 606/185 |
| 5,571,215 A | 11/1996 | Sterman et al. | | 623/66 |
| 5,584,796 A | 12/1996 | Cohen | | 600/201 |
| 5,588,949 A | 12/1996 | Taylor et al. | | 600/166 |
| 5,588,951 A | 12/1996 | Zhu et al. | | 600/207 |
| 5,591,192 A | 1/1997 | Privitera et al. | | 606/185 |
| 5,598,280 A | 1/1997 | Nishio et al. | | 349/57 |
| 5,613,751 A | 3/1997 | Parker et al. | | 362/31 |
| 5,618,096 A | 4/1997 | Parker et al. | | 362/31 |
| 5,630,795 A | 5/1997 | Kuramoto et al. | | 604/30 |
| 5,759,150 A | 6/1998 | Konou et al. | | 600/114 |
| 5,775,791 A | 7/1998 | Yoshikawa et al. | | 362/31 |
| 5,779,338 A | 7/1998 | Ishikawa et al. | | 362/31 |
| 5,785,648 A | 7/1998 | Min | | 600/206 |
| 5,786,665 A | 7/1998 | Ohtsuki et al. | | 313/512 |
| 5,817,005 A | 10/1998 | Cohen | | 600/201 |
| 5,845,038 A | 12/1998 | Lundin et al. | | 385/901 |
| 5,876,107 A | 3/1999 | Parker et al. | | 362/31 |
| 5,891,013 A | 4/1999 | Thompson | | 600/104 |
| 5,895,115 A | 4/1999 | Parker et al. | | 362/511 |
| 5,913,818 A | 6/1999 | Co et al. | | 600/204 |
| 5,921,652 A | 7/1999 | Parker et al. | | 362/31 |
| 5,928,139 A | * 7/1999 | Koros et al. | | 600/205 |
| 5,961,198 A | 10/1999 | Hira et al. | | 362/31 |
| 5,967,971 A | 10/1999 | Bolser | | 600/211 |
| 5,982,969 A | 11/1999 | Sugiyama et al. | | 385/123 |
| 5,995,288 A | 11/1999 | Kashima et al. | | 359/599 |
| 6,033,361 A | 3/2000 | Co et al. | | 600/210 |
| 6,079,838 A | 6/2000 | Parker et al. | | 362/31 |
| 6,129,662 A | 10/2000 | Li et al. | | 600/182 |
| 6,139,493 A | 10/2000 | Koros et al. | | 600/215 |
| 6,176,824 B1 | 1/2001 | Davis | | 600/178 |
| 6,185,356 B1 | 2/2001 | Parker et al. | | 385/133 |
| 6,196,968 B1 | 3/2001 | Rydin et al. | | 600/210 |
| 6,210,325 B1 | 4/2001 | Bartie et al. | | 600/229 |
| 6,228,025 B1 | 5/2001 | Hipps et al. | | 600/213 |
| 6,304,712 B1 | 10/2001 | Davis | | 385/147 |
| 6,322,499 B1 | 11/2001 | Evans et al. | | 600/212 |
| 6,427,034 B1 | 7/2002 | Meis et al. | | 385/14 |
| 6,504,985 B2 | 1/2003 | Parker et al. | | 385/133 |
| 6,551,346 B2 | 4/2003 | Crossley | | 607/88 |
| 6,554,768 B1 | 4/2003 | Leonard | | 600/213 |
| 6,565,225 B2 | 5/2003 | Mabuchi et al. | | 362/31 |
| 6,817,978 B2 | 11/2004 | Holland et al. | | 600/212 |
| 6,893,394 B2 | 5/2005 | Douglas et al. | | 600/205 |
| 6,910,783 B2 | 6/2005 | Mezei et al. | | 362/31 |
| 7,223,233 B2 | 5/2007 | Branch et al. | | 600/212 |
| 2004/0172105 A1 | 9/2004 | Vankoski et al. | | 607/88 |
| 2005/0159651 A1 | 7/2005 | Raymond et al. | | 600/213 |
| 2005/0165283 A1 | 7/2005 | Hestad et al. | | 600/212 |
| 2005/0182301 A1 | 8/2005 | Acker et al. | | 600/204 |
| 2006/0069314 A1 | 3/2006 | Farr | | 600/179 |
| 2006/0224045 A1 | 10/2006 | Whipple et al. | | 600/245 |

FOREIGN PATENT DOCUMENTS

| | | | |
|---|---|---|---|
| GB | 1435600 | 5/1976 | |
| GB | 2078526 | 1/1982 | 17/2 |
| GB | 2133694 | 8/1984 | 17/2 |
| WO | WO96/17206 | 6/1996 | |
| WO | WO96/37730 | 11/1996 | |
| WO | WO00/50807 | 8/2000 | |

* cited by examiner

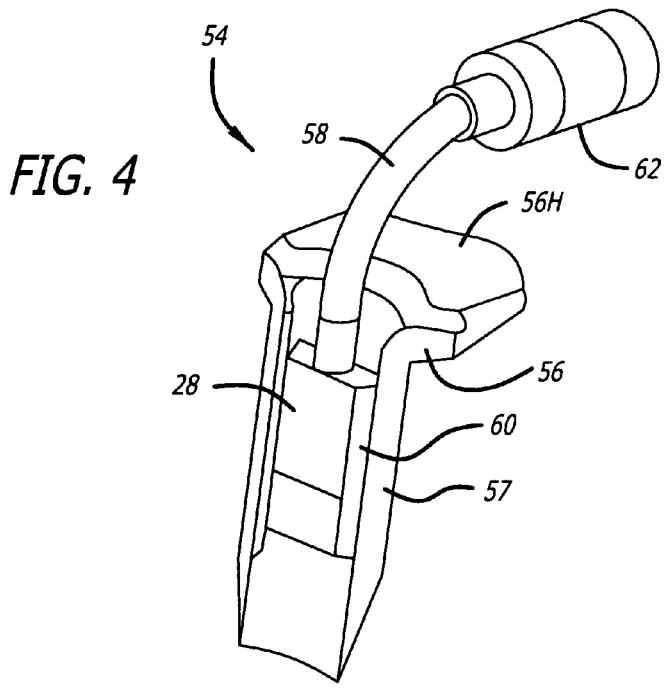
FIG. 4
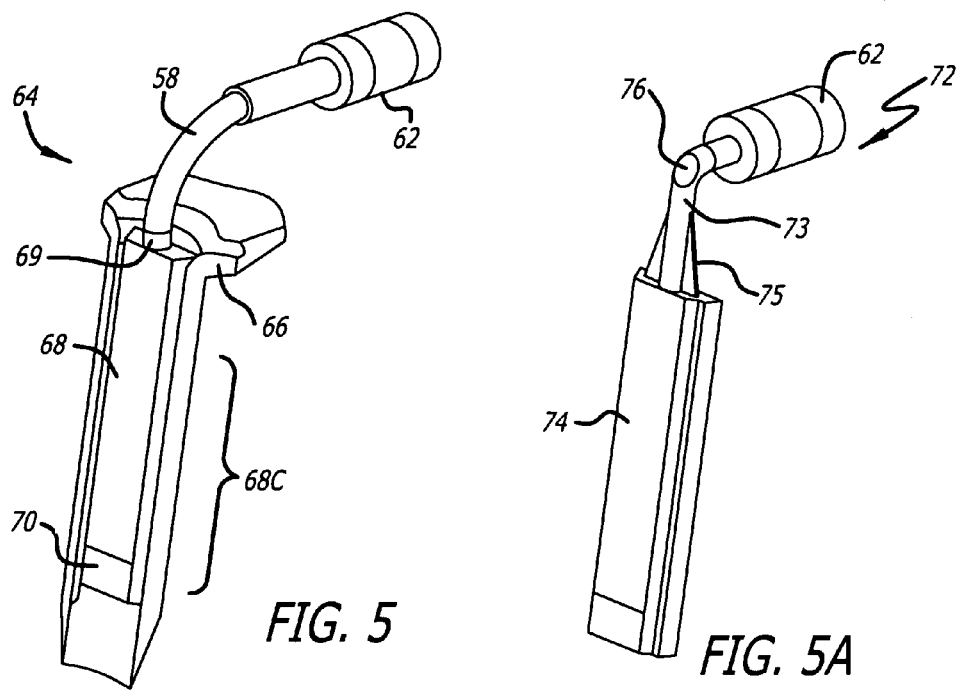
FIG. 5
FIG. 5A

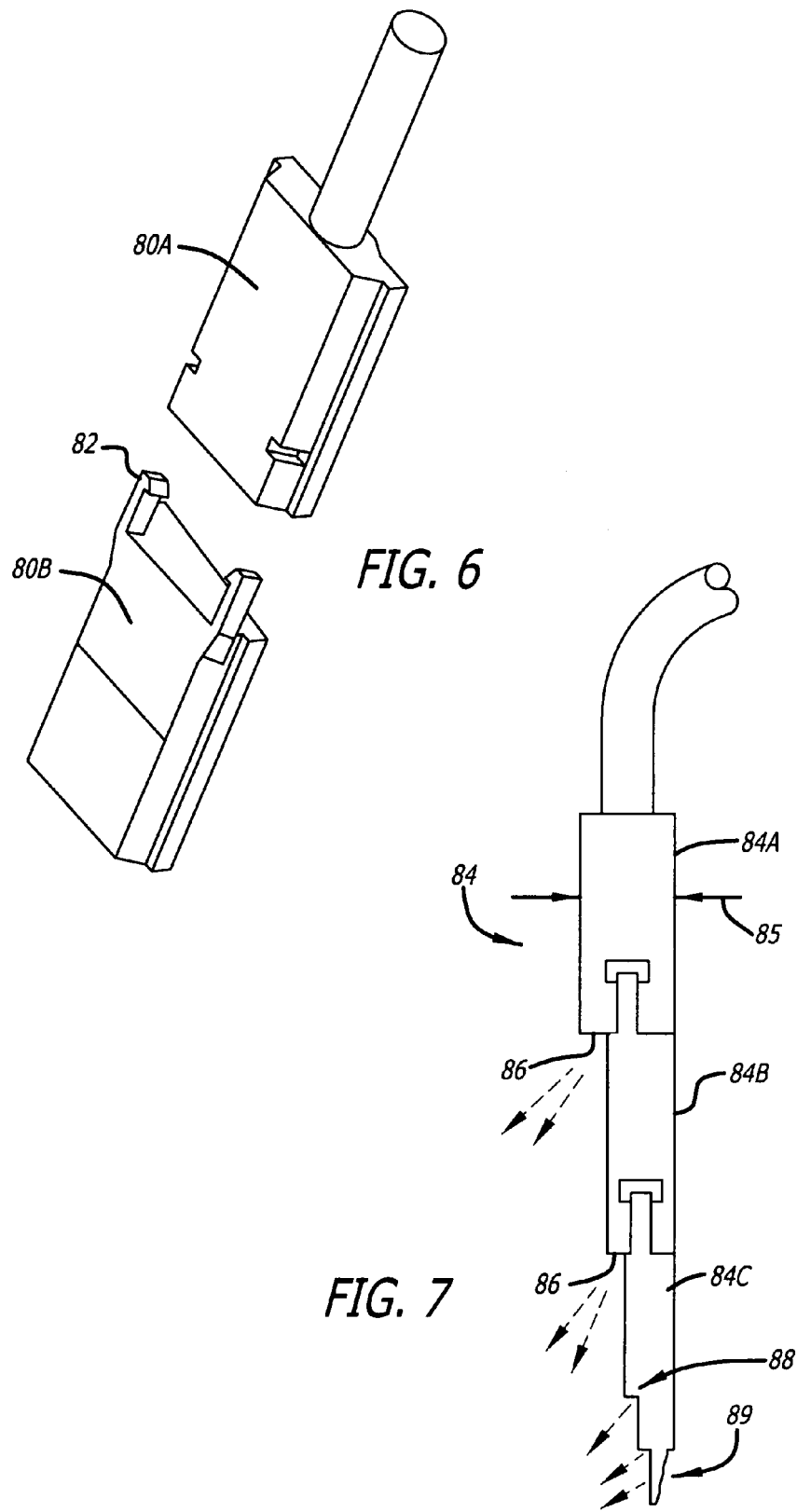

BLADE INSERT ILLUMINATOR

RELATED APPLICATIONS

This application claims priority from U.S. Provisional patent application 60/808,877 filed May 26, 2006.

FIELD OF THE INVENTION

The inventions described below relate to the field of medicine and more specifically, to providing in vivo surgical field illumination during surgical procedures.

BACKGROUND OF THE INVENTION

Surgical procedures often employ the use of retractors to separate and hold tissue to expose the underlying tissue on which the procedure is to be performed. Blade retractors are a type of retractor that typically have a flat or slightly curved blade that is inserted into the body. The blade may have a handle portion that is used to manipulate the blade. One or more blade retractors may be used in a surgical procedure. Illumination in these procedures is typically limited to external illumination sources such as ceiling or wall mounted lights or light sources integrated into a headband worn by the surgeon (e.g., LED based or fiber optic based). These light sources provide poor illumination of the deep tissue on which surgery is to be performed. Fiber optic devices may be fixed to a blade retractor to shine light on the deep tissue, but fiber optic systems either provide a small spot of light requiring constant repositioning to view all the tissue, or they provide a very diffuse light that does not adequately illuminate the tissue of interest. The fiber optic also has a very small emission area. Any debris or blood that covers it will block the majority of illumination. Furthermore, fiber optic devices are very expensive, requiring specialized cutting, grinding and polishing. Some blade retractors are provided with lengthwise channels into which ancillary retracting or illumination devices may be inserted. Blade insert illumination devices are currently limited to fiber optic approaches with their poor illumination characteristics.

SUMMARY

A blade insert illuminator may comprise one or more illuminator sections designed to engage a mating channel or channels formed in the blade. The illuminator is preferably made from a suitable light conducting plastic material such as acrylic or polycarbonate or silicone. Blade insert illuminators may be characterized by having a light input portion, a light conducting portion and a light output portion. The blade illuminator may be oriented at any suitable position along the retractor blade channel.

The light input portion of a blade insert illuminator receives light from an external light source. Such a light source may be an external light box, e.g., a xenon light box, to which one end of a fiber optic light guide cable is attached to conduct light to the surgical field. In this instance, the other end of the fiber optic cable would be the source of light for the blade insert illuminator, for example, by employing a mating connector on the illuminator so that it may connect to the fiber optic cable. The light input portion may include a short section of a light conducting material, such as for example, a suitable plastic or a fiber optic bundle, that is permanently integrated or temporarily attached.

The light conducting portion of a blade insert illuminator typically is responsible for conducting light from the light input section to the light output section. It may be simply a section of optical material designed to support total internal reflection that is integral with the light input and light output portions. Any suitable surface treatment, such as for example, polishing, reflective coating, anti-reflective (AR) coatings and or dielectric coatings may be used to support total internal reflection.

The light output portion of a blade insert illuminator contains specially designed output optical structures that allow light to be extracted from the illuminator to shine onto a predetermined area of interest. Such structures may be molded into the light output portion or such structures may be applied, for example, as a film.

A blade insert illumination system may consist of a single illuminator that contains the light input, light conducting and light output portions in a simple, single device that acts as a waveguide. Such a system may also be comprised of different sections of illuminator components that attach together to form a complete system. In this case, there may be a light input section designed to receive light from a light source, one or more light conduit sections designed to conduct light from the light input section to a light output section, and a light output section containing the optical output structures that allow light to escape and illuminate a predetermined area of interest, said sections attaching together to form a complete system. Each section acts as a waveguide and may employ optical structures to polarize and or filter the light energy entering or exiting the waveguide.

A blade insert illuminator must be designed and fabricated to maximize light transfer from the light source or fiber optic input cable and minimize light loss from the waveguide in order to provide an efficient light transmission system. Efficiency is particularly important for LED and other light sources, e.g., halogen or xenon lamps, because it directly determines the required brightness of the LED. An inefficient waveguide experiences significant light loss, typically 60% of light may be lost from input to output. Such a light guide would require a high power LED to provide sufficient light. A high power LED requires a lot of power and generates significant heat, thereby requiring large batteries and bulky and inconvenient heat sinking devices and methods that add to the size and increase the difficulty of using such a device. Other high power light sources often require noisy fans, which may disturb the medical personnel conducting a surgery or medical exam. Lamps used in high power light sources have a limited life time, requiring frequent and expensive replacement, due to the need to drive the lamp at high power levels to generate enough light. An efficient waveguide, one in which light loss is typically less than 30%, allows a much lower power LED or other light source to be used, thereby significantly reducing or eliminating the need for special heat sinking devices and methods, reducing cost, and improving the usability of the device. The design of an efficient blade insert illumination waveguide may involve special design of the light input portion of the waveguide to efficiently capture the incoming light, for example, by careful selection of numerical apertures or using a lens, design and fabrication of the light reflecting walls of the light conducting portion of the waveguide to maintain surface finish to maximize reflection and reduce light lost through refraction, the use of reflective or dampening coatings, the design of light directing optical structures that direct the light toward the light output optical structures while minimizing light loss through refraction, and or the design of light output optical structures that maximize light exiting the waveguide through refraction, particularly refraction of light in certain directions, while minimizing light lost through reflection.

A blade insert illumination system includes one or more illumination elements composed of a transparent or semi-transparent polymer that is preferably biocompatible and sterilizable. The illumination elements operate as a waveguide and may incorporate optical components such as, for example, symmetric or asymmetric facets, lenses, gratings, prisms and or diffusers to operate as precision optics for customized delivery of the light energy. The illumination elements may be modular, allowing components to be mixed and matched for different sizes of blade retractors, or may be a single integrated unit. Each module may also have different performance characteristics such as a diffuse light output or a focused light output allowing users to mix and match optical performance as well.

BRIEF DESCRIPTION OF THE DRAWINGS

FIG. 4 is a perspective view of a single waveguide blade illuminator with a flexible input coupling for a short blade retractor.

FIG. 5 is a perspective view of a single waveguide blade illuminator system with a flexible input coupling for a long blade retractor.

FIG. 5A is a perspective view of an alternate waveguide blade illuminator with a rigid input coupling.

FIG. 6 is a perspective view of an alternate attachment mechanism for blade insert illuminator sections.

FIG. 7 is a side view of blade insert illuminator with stepped waveguide sections.

DETAILED DESCRIPTION OF THE INVENTIONS

Figures 1, 1A, 1B:
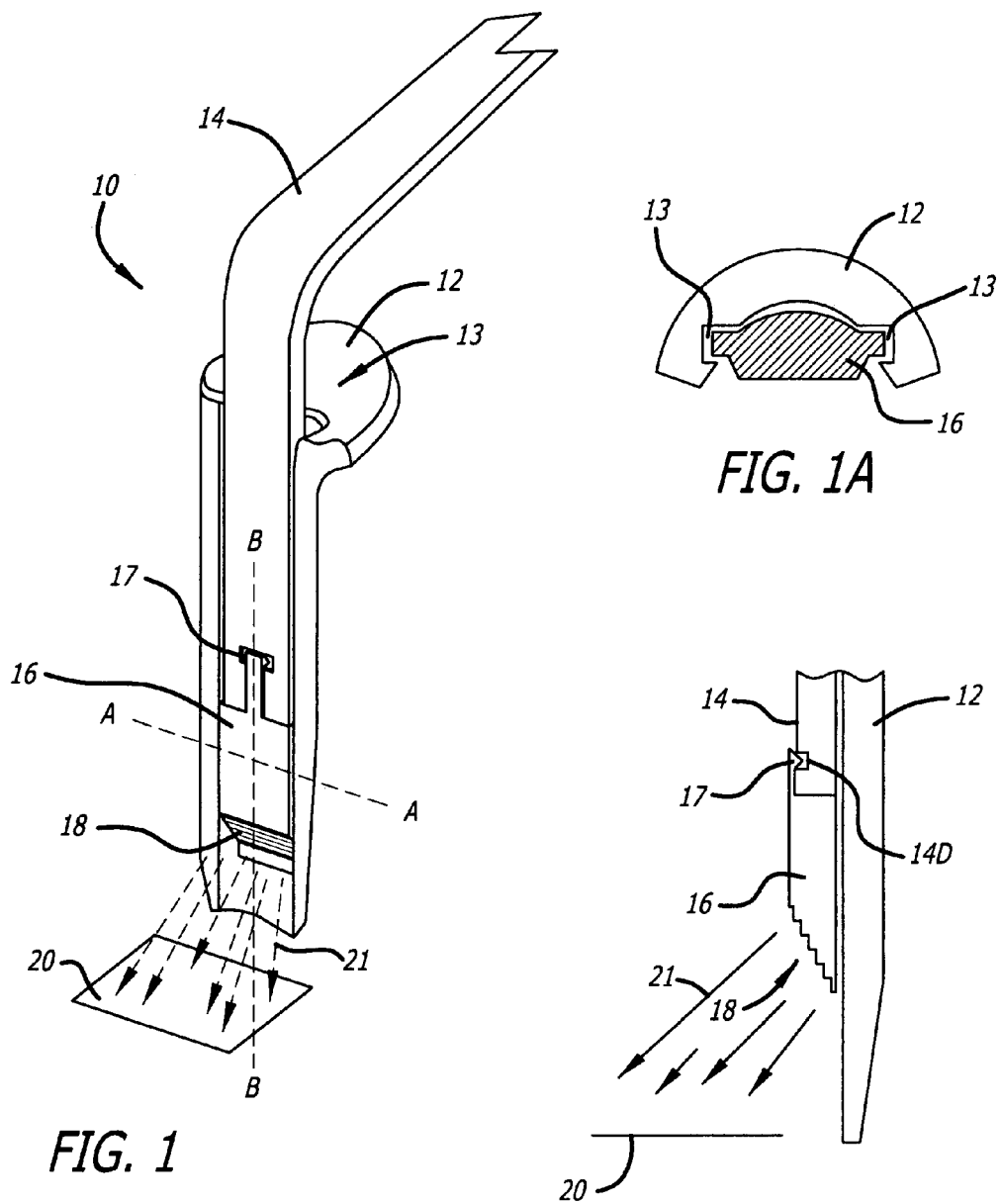
FIG. 1 is a perspective view of a blade insert illuminator.
FIG. 1A is a cross-section of the blade insert illuminator of FIG. 1 taken along A-A.
FIG. 1B is a cross-section of the blade insert illuminator of FIG. 1 taken along B-B.

Retractor illumination system 10 of FIG. 1 includes blade retractor 12 including channel 13 to engage a fiber optic input 14 and waveguide illuminator 16. Latch 17 serves to mechanically attach waveguide illuminator 16 to fiber optic input 14 so that the resulting assembly may be moved up and down in channel 13 to any position suitable for illumination. The optical coupling between fiber input 14 and waveguide illuminator 16 is a simple face-to-face coupling, which may be enhanced by use of an index matching gel, or other similar material, applied to either the fiber input 14 or the waveguide illuminator 16 or both. Light entering waveguide illuminator 16 is contained within the waveguide with minimal light loss until it reaches output optical structures such as output structures 18, where light exits to illuminate the predetermined illumination area 20. Output optical structures 18 may include one or more stair stepped facets or lenses that may include a radius or angled face, one or prism structures, one or more diffraction gratings, applied optical film, or other optical structures designed to direct the available light to the predetermined illumination area 20.

In the cross-section view of FIG. 1A channels 13 of blade 12 engage waveguide illuminator 16. Any suitable channel configuration may be used, such as, for example, a single channel with a circular or rhomboid cross-section. The section view of FIG. 1B shows a section of blade retractor 12, waveguide illuminator 16 and fiber input 14, with detail showing latch 17 which snaps into a hole or detent 14D formed in fiber input 14 and the latch may be disengaged with a minor amount of force. Output optical structures 18 control and direct output light energy 21 which illuminates predetermined illumination area 20.

Figure 2:
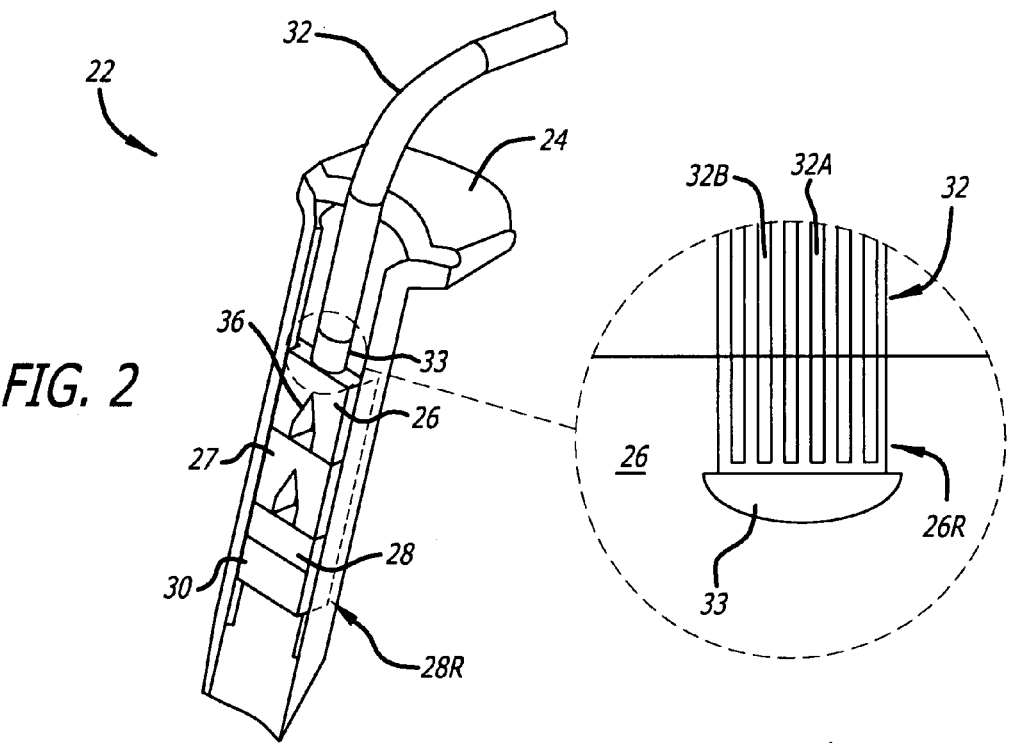
FIG. 2 is a perspective view of an alternate blade insert illuminator.

Alternate blade insert illumination system 22 of FIG. 2 includes blade retractor 24 that includes light input section 26, one or more light conduit sections such as light conduit section 27, and a light output section such a light output section 28 that includes one or more output optical elements such as output optical elements 30. In this configuration, light input section 26 has an integrated fiber optic input 32. One or more fiber optic strands such as strands 32A and 32B may be integrated into the upper portion of light input section 26 by molding the strands into light input section 26, gluing the strands into a formed receiving hole 26R formed into the section, or other suitable methods. A light coupling element such as element 33 may also be included to improve light coupling and distribution. A collar such as collar 34 may be provided to aid in strain relief for the optical fiber input. Light directing structure 36 causes the light coming into the center of the waveguide illuminator to be directed along the sides of light input section 26. The same light directing structure is shown in light conduit section 27, serving to direct the light down to the next section. Light input section 26 and light conduit section 27 may be provided without the light directing structure, but this may result in a decrease in efficiency.

Output optical element 30 may have a flat face to which an optical output film is applied to allow light to escape and direct the light toward tissues of interest, or output section 28 may have output optical film or molded structures located on or integrated into rear face 28R that serve to send light out through output optical element 30.

Figure 2A:
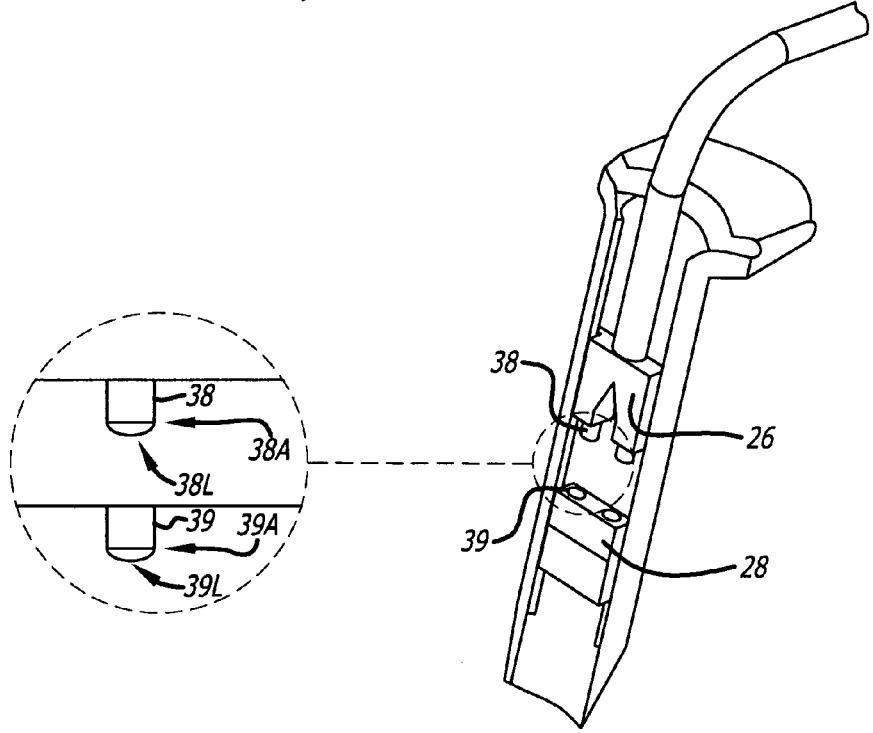
FIG. 2A is a perspective view of the attachment mechanism of the blade illuminator of FIG. 2.

FIG. 2A shows the blade insert illuminator system of FIG. 2 with light conduit section 27 removed to show the section attachment mechanism consisting of one or more male members such as engagement member 38 and a corresponding receptacle such as receptacle 39. Output end 38A of the male member 38 may also include one or more output transmission coupling structures or optical structures, e.g., a lens, such as lens 38L to focus the light into the corresponding receptacle. Bottom 39A of receptacle 39 may also include one or more input transmission coupling structures or optical structures, e.g., a lens, such as lens 39L to spread light into its corresponding waveguide. In use, the male members are pressed into the female receptacles of the subsequent section and friction holds the sections together.

In this configuration, light conduit section 27 of FIG. 2 may be removed, allowing light input section 26 and light output section 28 to be directly connected together, for example, to fit a blade having a short length or to permit adjustment along the blade retractor of the waveguide element to adjust the location of the illumination area. One or more light conduit sections 27 may be added to the assembly to fit blades of medium or long length thereby providing a modular blade insert illumination system whose components may be mixed and matched as needed. For example, if more than one blade retractor is used in a procedure, one blade may be fitted with a shorter assembly of blade illumination components to illuminate the upper part of the surgical field and a second blade may be fitted with a longer assembly of blade illumination system components to illuminate the lower, deeper part of the surgical field. Sliding a blade insert illumination system up and down slightly within the blade channel allows the illumination area to be adjusted, for example, sliding the light output section closer to the work area increases the intensity of illumination and sliding it away from the work area provides a more diffuse, less intense illumination. In this way, the modular blade insert illumination system may be optimized for a particular type of work to be performed.

Figure 3:
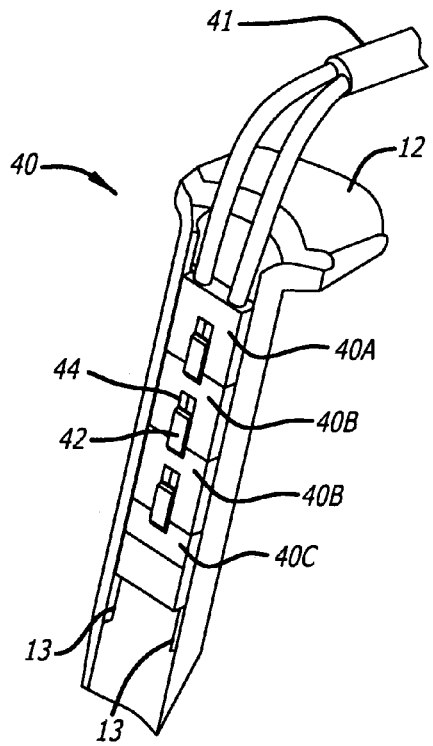
FIG. 3 is a perspective view of another blade insert illuminator.

FIG. 3 illustrates an alternate blade insert illumination system 40 inserted into blade 12. Blade insert illumination system 40 includes light input section 40A, one or more light conduit sections such as conduit sections 40B and light output section 40C. Bifurcated fiber optic cable 41 is integrated into light input section 40A. This blade illuminator configuration includes an engagement arm 42 and light directing structure 44.

Figure 3A:
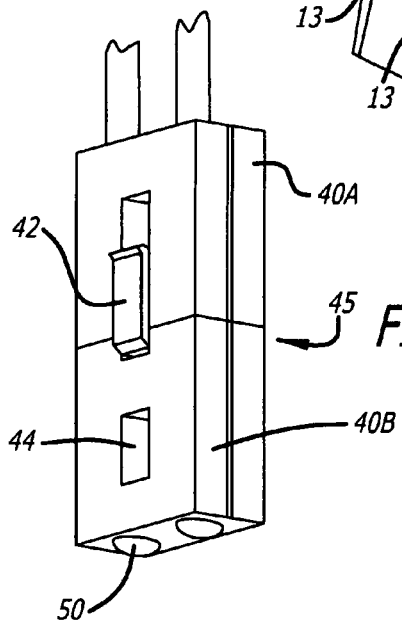
FIG. 3A is a close perspective view of the light output section of the blade illuminator of FIG. 3.
Figure 3B:
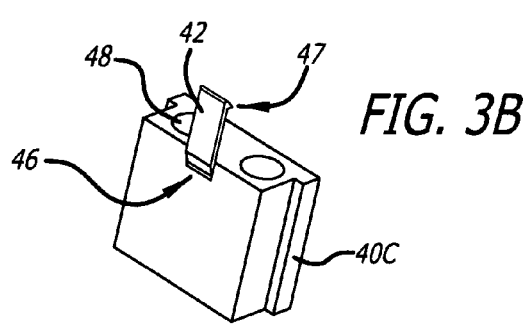
FIG. 3B is a close perspective view of a conduit section of the blade illuminator of FIG. 3.
Figure 3C:
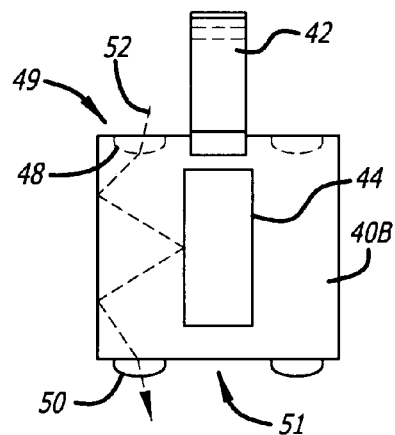
FIG. 3C is a front view of a light ray path for a light conduit section of the blade illuminator of FIG. 3.

FIGS. 3A, 3B and 3C illustrate details of arm 42 and light directing structure 44. When two or more modular elements of blade insert illuminator system 40 engage channels 13, the engagement arm 42 of first element 40B engages adjacent element 40A to maintain a secure optical connection at interface 45 between the elements. Arm 42 is a generally resilient member to permit flexing at joint 46 which permits tooth 47 to engage the light directing structure of the adjacent element. One or more light control elements such as light collecting lens 48 may be included at the input end of each blade illuminator element such as input end 49 of light output section 40C. Similarly, light output lens 50 may be included at the bottom, exit or output end 51 of a light conduit section such as conduit section 40B. Lenses 48 and 50 are illustrative of the use of optical structures to aid in the transmission of light between modules. Any other suitable optical structures such as angled facets, multi-faceted lens structures, spherical or aspherical lens may also be used. FIG. 3C illustrates how light travels in a blade insert illuminator conduit such as conduit element 40B. Light from bifurcated fiber optic cable 41 first enters the top of light input section 40A as illustrated in FIG. 3. Light energy 52 entering a blade illuminator waveguide such as conduit 40B, either from the fiber optic cable or light collecting lens 48, are guided by light directing structure 44 and light output lens 50.

Single element blade illuminator 54 is shown in FIG. 4. In this example, retractor 56 has a short blade 57. When used with a retractor having a long blade, single element blade illuminator 54 may be adjusted along the length of the retractor blade to provide illumination wherever it is needed.

In this configuration, a short section of fiber optic cable 58 is integrated into blade illuminator waveguide 60 at the output end and has any suitable connector 62 such as an industry standard ACMI connector or any other type of standard or proprietary connector, at the input end. Connector 62 is normally connected to a standard fiber optic light guide cable that conducts light from an external light source. Since blade insert illumination system 54 is made to minimize light loss, portable LED light sources may be attached directly to connector 62 or via a much shorter fiber optic light guide cable. Short section of fiber optic cable 58 is flexible and allows considerable latitude in how the connector 62 and light guide cable are oriented. For example, the connector 62 may be placed toward handle 56H of retractor 56 or it may be placed on either side in order to keep out of the way of the surgeon and any other equipment that may be in use.

Single element extended blade illuminator system 64 of FIG. 5 is a simple blade insert illuminator designed to fit long blade retractors such a retractor 66. Illuminator waveguide 68 receives light at input 69, conducts light through total internal reflection throughout center portion 68C, and output optical structures such as output structure 70 directs the light toward a predetermined area to be illuminated.

FIGS. 4 and 5 illustrate that a blade insert illuminator may be provided in different sizes appropriate for the size of the retractor blade with which it is to be used. Blade insert illuminator 72 of FIG. 5A is an extended waveguide blade illuminator with a rigid light input component 73 in the place of the short section of fiber optic cable 58 as shown in FIGS. 4 and 5. Rigid light input component 73 allows all of the light guiding sections, waveguide 74 and rigid light input component 73, to be molded as one device, thereby reducing cost of the assembly. Support gussets or flanges such as flanges 75 may be added to provide stability. Flanges 75 may have a coating or film applied to prevent light from escaping or may be made from a different material, for example, using a co-molding or overmolding process. Rigid light input component 73 may have an orthogonal input as shown, requiring light directing structure 76 to direct light from connector 62 down to waveguide 74 of the waveguide illuminator. Rigid light input component 73 may also be formed with a radius, as shown in FIG. 5, and using total internal reflection to guide the light from connector 62 to the body of the waveguide. Rigid light input component 73 may also be made rotatable, thereby allowing the fiber optic light guide cable to be positioned as needed around the surgical field to avoid interference with other instruments.

FIG. 6 illustrates alternate modular blade insert illuminator elements 80A and 80B showing an alternative placement of latches 82 that hold the waveguide components together. Keeping the latches off to the side of the components, rather than in front as shown in FIG. 3, reduces the likelihood of the latches being accidentally disengaged or broken by surgical instruments during the course of a surgical procedure. Any other suitable mechanisms may be used to attach the modular components to each other, e.g., dovetail joints, tongue-and-groove joints, adhesives that are preferably index matching adhesives, etc., to optimize light coupling from one module to the next. The attachment mechanisms may also be separate from the optical path, for example, metal pins and sockets may be located in optically inactive areas of the modules.

FIG. 7 is a side view of an alternate modular blade insert illumination system 84 wherein each subsequent waveguide section is lessened in thickness 85. This allows output optical structures such as output structures 86 to be placed at the exposed end of the upstream waveguide, thereby allowing light to be directed from each waveguide section such as sections 84A, 84B, 84C. Each waveguide component such as sections 84A, 84B may have a bottom surface that contains output optical structures 86 over much of its surface to act as a terminal illumination component in case no other subsequent waveguide components are attached. Light output section 84C shows stepped output optical structure 88 on the front side and output optical structures 89 on the back side. Without output optical structures 88 that direct light out of the face, light would be lost out the end of light output section 84C, therefore, the combination of output optical structures 88 and 89 contribute to higher efficiency through less lost light.

Figure 8:
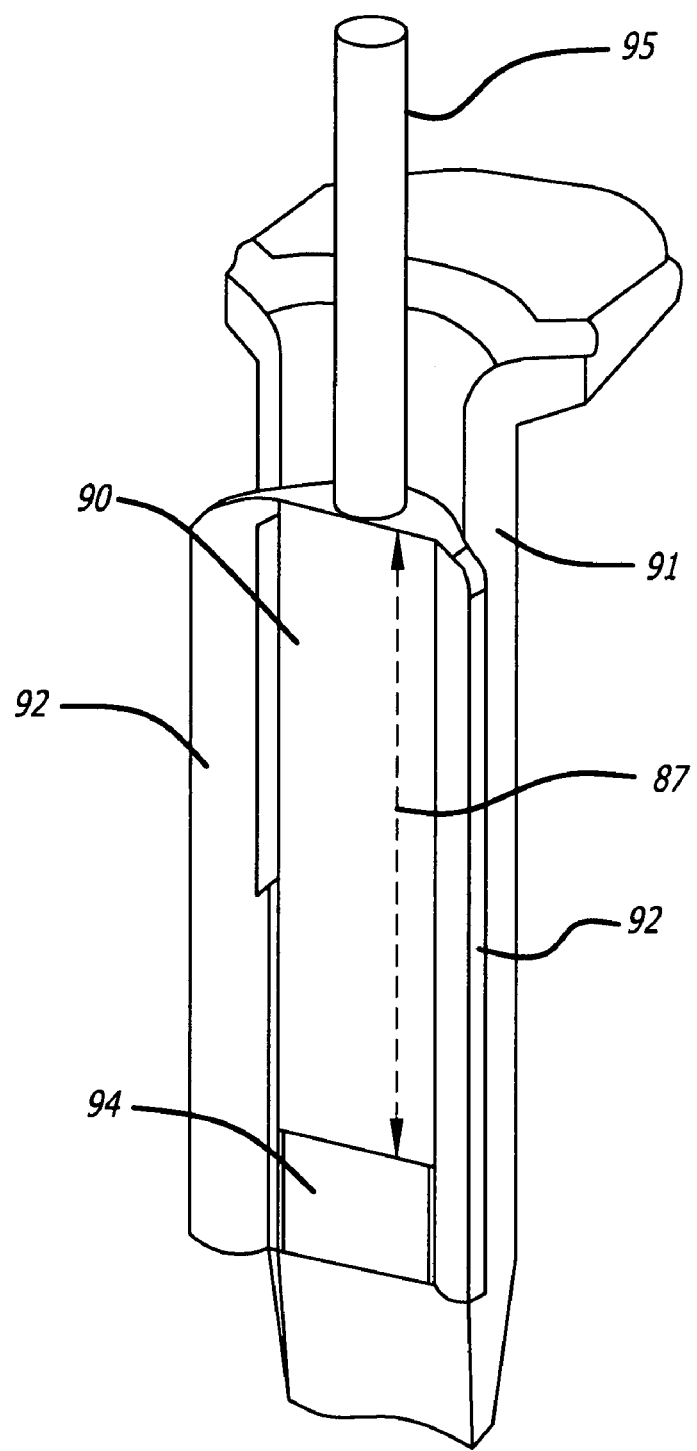
FIG. 8 is a perspective view of an alternate single waveguide blade insert illumination system.

Referring now to FIG. 8, winged blade insert illuminator 90 is shown engaged to retractor 91. Illuminator 90 has integrated wings 92 that may serve an additional retracting function. Wings 92 are oriented generally parallel to long axis 87 of illuminator 90. In this configuration, light is directed to exit output optical structure 94. Light enters illuminator 90 via light input component 95, which may be a fiber optic component or a rigid light conducting component at previously discussed. Because total internal reflection may allow light to enter wings 92, the wings may need a reflective coating to prevent light from exiting the wings and being lost or shining into unwanted directions, such as back into the surgeons eyes.

Figure 9:
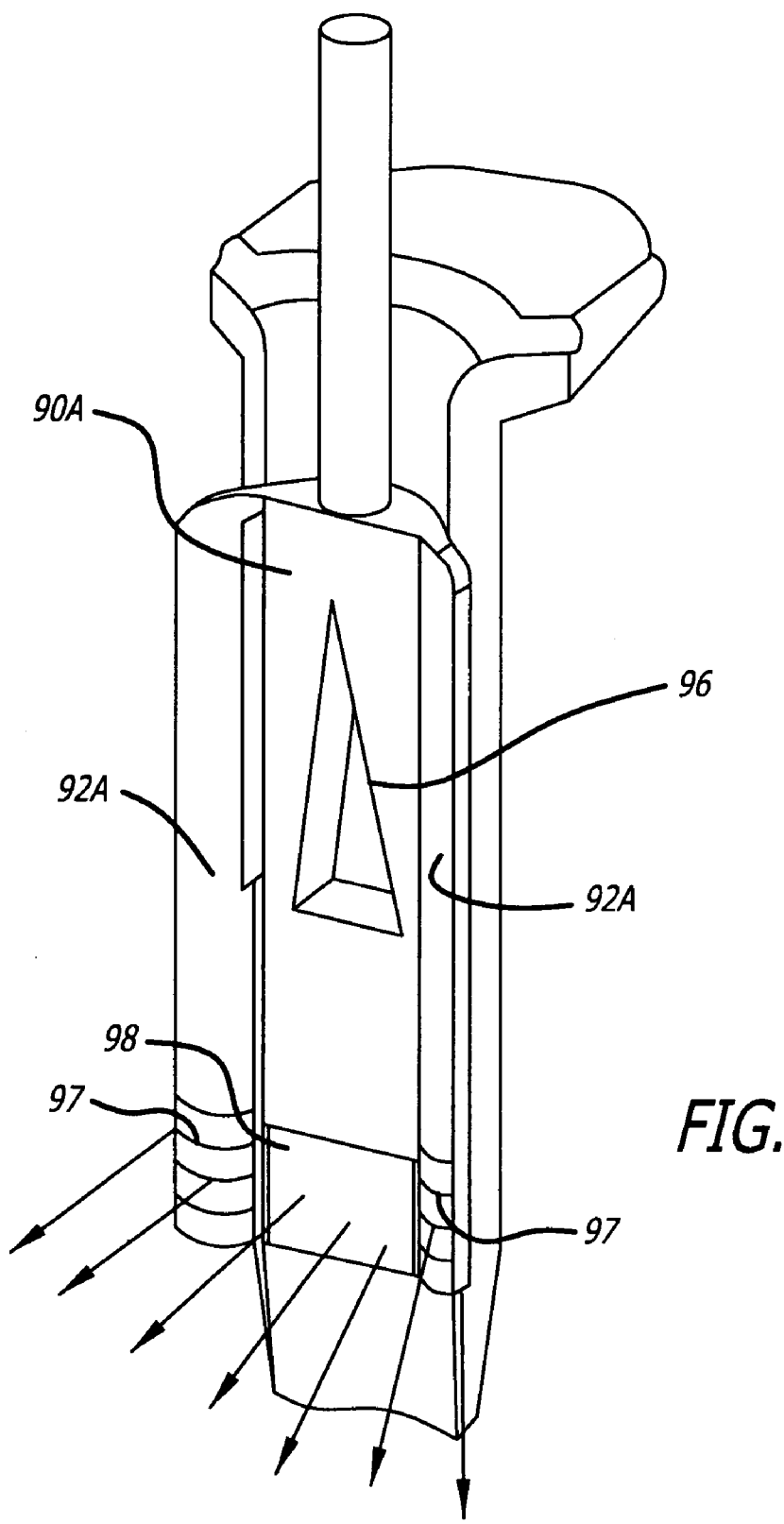
FIG. 9 is a perspective view of a single waveguide blade insert with a light directing structure.

FIG. 9 illustrates another alternate blade insert illuminator 90A that has a light directing element 96, which serves to direct the light coming into the middle of the illuminator out toward the wings 92A. Output optical structures such as structures 97 and 98 may be placed on wings 92A and body respectively to provide illumination from both structures as shown by the arrows.

Figure 10:
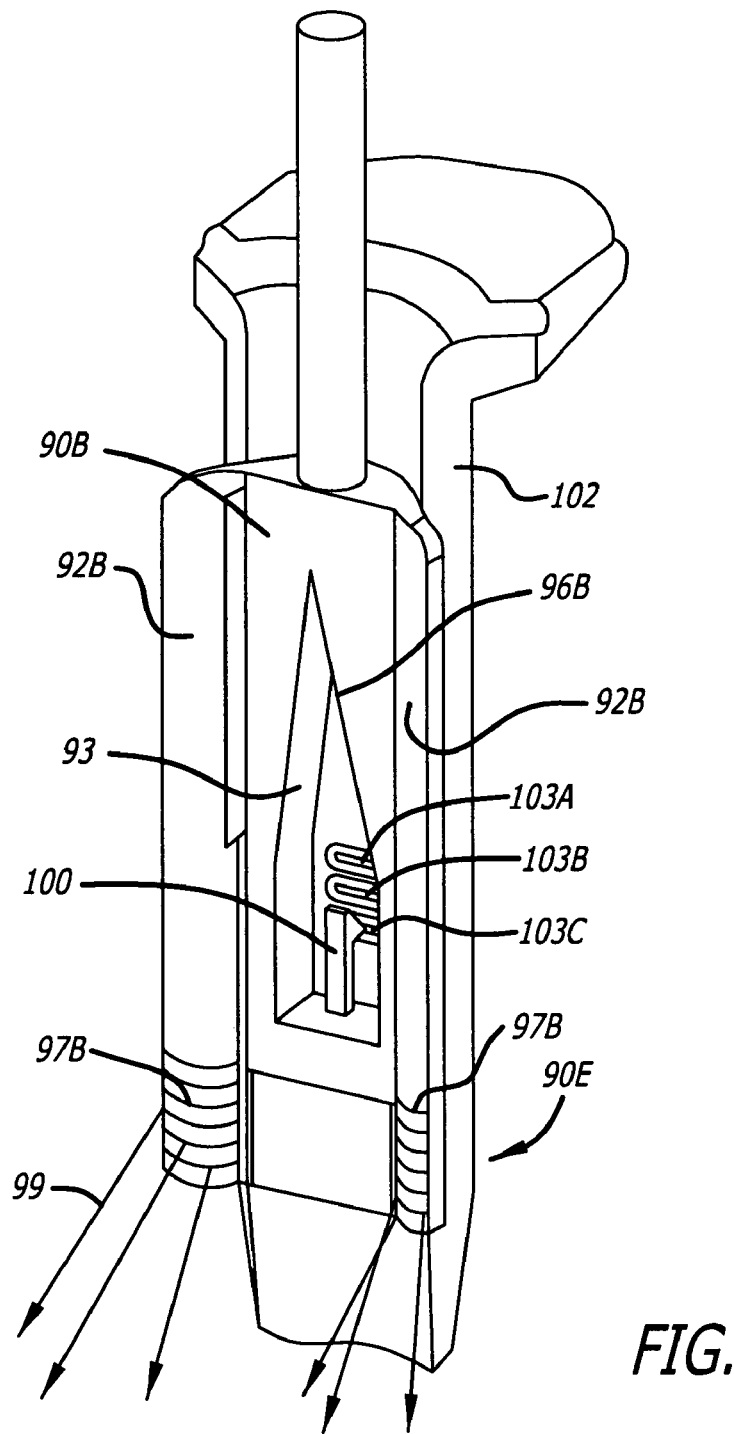
FIG. 10 is a perspective view of a single waveguide blade insert with a light directing structure with an attachment mechanism.

FIG. 10 illustrates another alternate blade insert illuminator 90B with an extended light directing element 96B. In this embodiment, optical output structures are placed only on the wings 92B so that illumination, light energy 99, only exits through extended output structures 97B in wings 92B as shown by the arrows. Extended light directing element 96B has reflective walls such as wall 93 that extend to output end 90E of illuminator 90B to maximize light reflected to the wings 92B. This configuration also includes alternative latch arm 100 oriented near the interface with retractor 102 to engage cutouts or detents such as detents 103A, 103B and 103C located in retractor 102. Latch arm 100 maybe made of the same material as the waveguide or may be made of a different material for durability. For example, latch arm 100 may be made from steel or titanium and insert molded into illuminator 90B.

Alternatively, a retractor blade may be inserted into one or more slots in the illuminator waveguide to provide rigidity and or to enable cooperation with surgical site retention apparatus.

Figure 11:
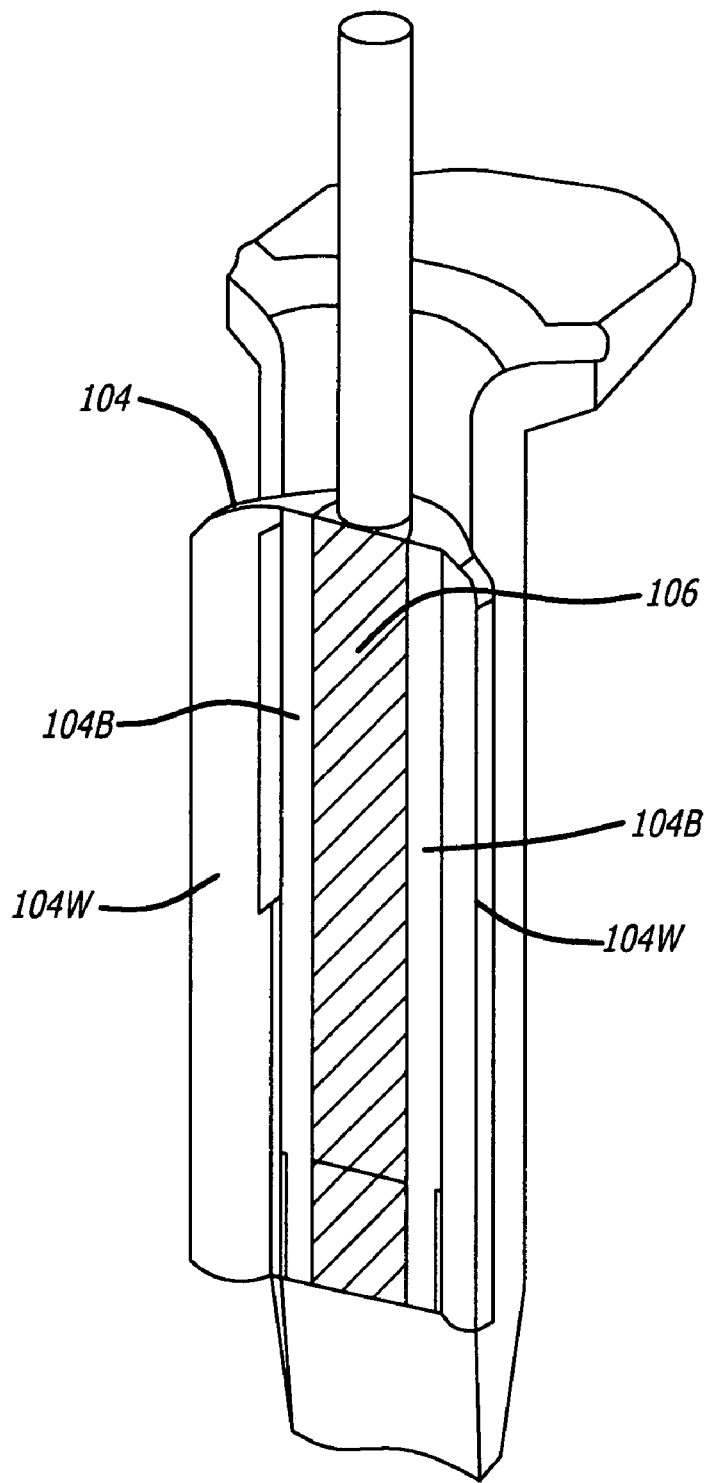
FIG. 11 is a perspective view of a single waveguide blade insert with a waveguide element co-molded with a retracting element.

Comolded blade insert illuminator 104 of FIG. 11 includes waveguide section 106 has been co-molded or over-molded with wing and body retractor portions 104W and 104B respectively, which are made of a different material. For example, retractor wing and body portions 104W and 104B may be made of a stronger, glass reinforced plastic or steel or titanium for strength while waveguide section 106 is molded from a suitable optical material such as acrylic, polycarbonate, silicone or other similar optical materials.

While the preferred embodiments of the devices and methods have been described in reference to the environment in which they were developed, they are merely illustrative of the principles of the inventions. Other embodiments and configurations may be devised without departing from the spirit of the inventions and the scope of the appended claims.

We claim:

1. A modular retractor illumination system comprising: a blade retractor having two generally parallel channels for engaging a blade insert illuminator system; and a blade insert illuminator system adjustably engaging the channels of the blade retractor, the blade insert illuminator system including an input element with a light input coupling, a plurality of light conduit sections, and an output element with one or more light output structure, wherein the plurality of light conduit sections are disposed in the parallel channels and also disposed between the light input element and the output element, and wherein the plurality of light conduit sections are arranged such that light is directed from a first light conduit section to an adjacent second light conduit section, wherein adjacent light conduit sections are engaged together with an engagement arm thereby maintaining a secure optical connection between the adjacent light conduit sections, and each light conduit section acts as a wavequide and may employ optical structures to polarize and or filter the light energy entering or exiting the wavequide.

2. The modular retractor illumination system of claim 1 wherein the blade insert illuminator system further comprises:
    a light directing structure in each of the one or more conduit elements.

3. The modular retractor illumination system of claim 2 wherein the blade insert illuminator system further comprises:
    a light directing structure in the input element.

4. The modular retractor illumination system of claim 2 wherein the blade insert illuminator system further comprises:
    a light directing structure in the output element.

5. The modular retractor illumination system of claim 1 wherein the blade insert illuminator system further comprises:
    a light directing structure in each of the one or more conduit elements and the input element.

6. The modular retractor illumination system of claim 1 wherein the blade insert illuminator system further comprises:
    a light directing structure in each of the one or more conduit elements and the output element.

7. The modular retractor illumination system of claim 1 wherein the blade insert illuminator system further comprises:
    a light directing structure in each of the one or more conduit elements, the input element and the output element.

8. The modular retractor illumination system of claim 1, wherein the light input comprises a bifurcated fiber optical cable.

* * * * *